United States Patent
Hamasaki et al.

(10) Patent No.: US 10,959,916 B2
(45) Date of Patent: Mar. 30, 2021

(54) PRODUCTION METHOD FOR EASY-TO-TAKE SOLID PREPARATION (NUCLEATED TABLET), AND EASY-TO-TAKE SOLID PREPARATION

(71) Applicant: DAICEL CORPORATION, Osaka (JP)

(72) Inventors: Momoko Hamasaki, Himeji (JP); Anan Sakaguchi, Himeji (JP); Tomohito Okabayashi, Himeji (JP); Takahiro Hiramura, Tokyo (JP)

(73) Assignee: DAICEL CORPORATION, Osaka (JP)

( * ) Notice: Subject to any disclaimer, the term of this patent is extended or adjusted under 35 U.S.C. 154(b) by 0 days.

(21) Appl. No.: 15/737,956

(22) PCT Filed: Jun. 28, 2016

(86) PCT No.: PCT/JP2016/069119
§ 371 (c)(1),
(2) Date: Dec. 19, 2017

(87) PCT Pub. No.: WO2017/002799
PCT Pub. Date: Jan. 5, 2017

(65) Prior Publication Data
US 2018/0153773 A1 Jun. 7, 2018

(30) Foreign Application Priority Data

Jun. 29, 2015 (JP) .............................. JP2015-129530

(51) Int. Cl.

| | | |
|---|---|---|
| *A61J 3/10* | (2006.01) | |
| *A61K 9/20* | (2006.01) | |
| *A61K 9/28* | (2006.01) | |
| *A61J 3/06* | (2006.01) | |
| *A61K 47/42* | (2017.01) | |
| *A61K 47/14* | (2017.01) | |
| *A61K 47/36* | (2006.01) | |
| *A61K 47/26* | (2006.01) | |
| *B30B 11/34* | (2006.01) | |
| *A61K 47/12* | (2006.01) | |
| *A61K 47/38* | (2006.01) | |
| *A61K 47/10* | (2017.01) | |

(52) U.S. Cl.
CPC . *A61J 3/10* (2013.01); *A61J 3/06* (2013.01); *A61K 9/2054* (2013.01); *A61K 9/2063* (2013.01); *A61K 9/2095* (2013.01); *A61K 9/2826* (2013.01); *A61K 47/10* (2013.01); *A61K 47/12* (2013.01); *A61K 47/14* (2013.01); *A61K 47/26* (2013.01); *A61K 47/36* (2013.01); *A61K 47/38* (2013.01); *A61K 47/42* (2013.01); *B30B 11/34* (2013.01)

(58) Field of Classification Search
CPC ................ A61J 3/10; A61K 9/20; A61K 9/28
See application file for complete search history.

(56) References Cited

U.S. PATENT DOCUMENTS

| | | | |
|---|---|---|---|
| 3,424,839 A | 1/1969 | Montandraud et al. | |
| 2014/0308359 A1 | 10/2014 | Kudou et al. | |
| 2014/0357567 A1 | 12/2014 | Macbeth et al. | |

FOREIGN PATENT DOCUMENTS

| | | |
|---|---|---|
| JP | 61-025559 | 2/1986 |
| JP | 09-104621 | 4/1997 |
| JP | 2000281562 | 10/2000 |
| JP | 2004000575 | 1/2004 |
| JP | 2004002348 | 1/2004 |
| JP | 2013132285 | 7/2013 |
| JP | 2014532704 | 12/2014 |
| WO | 2001026632 | 4/2001 |
| WO | 2013098268 | 7/2013 |

OTHER PUBLICATIONS

Supplementary European Search Report of Application No. EP 16 81 7907 dated Feb. 4, 2019.
International Search Report of International Application No. PCT/JP2016/069119 dated Aug. 23, 2016.

*Primary Examiner* — Zohreh A Fay
(74) *Attorney, Agent, or Firm* — Ping Wang; Morris, Manning & Martin LLP

(57) ABSTRACT

The purpose of present invention to provide a method for the production of an easy-to-take solid preparation, which is mainly characterized in that an outer layer-forming processing to provide an easy-to-take property is simply performed in a dry process without going through a wet condition so as to make the formed outer layer thicker; the easy-to-take solid preparation and the like.

The present invention relates to a dry-process method for the production of an easy-to-take solid preparation wherein an inner core tablet is coated with a compression-molded outer layer-forming agent comprising a gelling agent that will show slipperiness when it is brought into contact with water, comprising loading separately or simultaneously the inner core tablet and powder of the outer layer-forming agent to a mortar inner surface, the bottom end surface of an upper-pestle, and the top end surface of a lower-pestle, and subsequently compression-molding them; a powder composition for coating a solid preparation for use in the above method, which comprises the water-soluble polymer and water-soluble sugar or sugar alcohol.

8 Claims, No Drawings

PRODUCTION METHOD FOR EASY-TO-TAKE SOLID PREPARATION (NUCLEATED TABLET), AND EASY-TO-TAKE SOLID PREPARATION

This application is a national stage application of International Patent Application No. PCT/JP2016/069119, filed Jun. 28, 2016, which claims priority to Japanese patent Application No. 2015-129530, filed Jun. 29, 2015. The entirety of the aforementioned applications is incorporated herein by reference.

FIELD

The present invention relates to a method for the production of an easy-to-take solid preparation (a nucleated tablet), which is mainly characterized in that an outer layer-forming processing for obtaining an easy-to-take property is simply performed in a dry process, to the easy-to-take solid preparation and the like.

BACKGROUND

Taking properties of a preparation for oral administration have been previously improved for patients who have difficulty in swallowing, elderly people and children who have a weak swallowing ability and the like.

For example, the preparations are formulated into liquid or jelly preparation form in many cases. However, when a content of a main drug is high, it will be difficult to mask its taste. And, when an active ingredient such as a drug is unstable in water, it will be difficult to be formulated in any preparation form.

Accordingly, easy-to-take preparations have been recently developed for facilitating swallowing of the solid preparation, wherein the surface of the preparations is coated with a gelling agent so that they will show slipperiness and become slippery against mucous membrane and easy to swallow when they are brought into contact with water in oral cavity.

These techniques use processes such as, for example, 1) formulating gell into a tablet by freeze-drying of; 2) punching into a circle shape a film of gelling layers comprising a drug layer between them; 3) punching into a circle shape gelling film layers comprising a tablet between them; 4) spraying a coating solution for gelling on a tablet, and the like.

Patent Literature (PTL) 1 discloses a coating composition for use in an easy-to-take solid preparation, which comprises a first thickener of a metal-crosslinking thickener, a polyvalent metal compound, and a second thickener; a method for the production of a preparation for oral administration by spray-coating alcohol solution having the coating composition dispersed therein onto a drug core comprising an active ingredient; and the preparation for oral administration produced thereby.

Patent Literature (PTL) 2 discloses a method for molding a product having a core by using a molding material such as particulate as a starting material, and a rotary-type nucleated-tableting machine (compression molding means).

As such, the nucleated tablet has been already known in the art. However, it has been not yet known to produce a nucleated tablet provided with easy-to-take property in a dry-process by comprising a gelling agent in an outer layer without going through a wet condition.

RELATED ARTS

Patent Literatures

PTL 1: International Publication Pamphlet W2011/125798
PTL 2: Japanese Patent Application Publication Hei 2 (1990)-38079

SUMMARY

Problems to be Solved by the Invention

The conventional treatment with a gelling agent seen in the prior arts such as PTL 1 was complicated since it requires the preparation of a gelling agent solution, the transfer to a coating machine after the compression molding and the like. Furthermore, a functional or active ingredient cannot be used if their stability for a solvent used in these processes is low.

There has been a problem that it was difficult to form a thick coating layer when the gelling agent was coated.

Accordingly, an object of the present invention is to solve such technical problems in the arts, and to provide a method for the production of an easy-to-take solid preparation, which is mainly characterized in that an outer layer-forming processing to provide an easy-to-take property is simply performed in a dry process without going through a wet condition so as to make the formed outer layer thicker; the easy-to-take solid preparation and the like. The term "easy-to-take" generally means "easy to drink" or "easy to swallow", as the characteristics or property of the solid preparations and the like.

Neither of the above Patent Literature discloses or suggests such technical problems.

Means to Solve the Problem

The present inventors have earnestly studied to solve the above problems and completed the invention comprising the following aspects Thus, the present invention provides the following aspects.

[Aspect 1]

A dry-process method for the production of an easy-to-take solid preparation wherein an inner core tablet is coated with a compression-molded outer layer-forming agent comprising a gelling agent that will show slipperiness when it is brought into contact with water, comprising loading separately or simultaneously the inner core tablet and powder of the outer layer-forming agent to a mortar inner surface, the bottom end surface of an upper-pestle, and the top end surface of a lower-pestle, and subsequently compression-molding them.

[Aspect 2]

The method according to Aspect 1 wherein the inner core tablet is obtained by compression-molding a core-molding material in a dry process.

[Aspect 3]

The method according to Aspect 1 or 2 wherein the inner core tablet and the powder of the outer layer-forming agent are loaded after a lubricant has been applied to the mortar inner surface, and the surfaces of the upper-pestle and the lower-pestle.

[Aspect 4]

The method according to any one of Aspects 1-3, wherein the gelling agent comprises at least one kind of a water-soluble polymer.

[Aspect 5]

The method according to Aspect 4, wherein the water-soluble polymer is selected from the group consisting of sodium carboxylmethylcellulose, sodium alginate, carrageenan, xanthan gum and gelatin.

[Aspect 6]

The method according to Aspect 5 wherein the water-soluble polymer is sodium carboxylmethylcellulose.

[Aspect 7]

The method according to any one of Aspects 1-6, wherein the outer layer-forming agent further comprises a lubricant.

[Aspect 8]

The method according to Aspect 7, wherein the lubricant is selected from the group consisting of calcium stearate, magnesium stearate and sucrose fatty acid ester.

[Aspect 9]

The method according to any one of Aspects 1-8, wherein the outer layer-forming agent further comprises water-soluble sugar or sugar alcohol.

[Aspect 10]

The method according to Aspect 9, wherein the sugar or sugar alcohol is erythritol, xylitol, mannitol or maltitol.

[Aspect 11]

An easy-to-take solid preparation that is produced by the method according to Aspects 1 to 10.

[Aspect 12]

A powder composition for coating a solid preparation for use in the method according to Aspects 1-10, which comprises the water-soluble polymer

[Aspect 13]

The powder composition according to Aspect 12 wherein the water-soluble polymer is sodium carboxylmethylcellulose.

[Aspect 14]

A powder composition for coating a solid preparation for use in the method according to Aspect 9 or 10, which comprises the water-soluble polymer and water-soluble sugar or sugar alcohol.

[Aspect 15]

The powder composition according to Aspect 14 wherein the water-soluble polymer is sodium carboxylmethylcellulose, and the sugar alcohol is erythritol or xylitol.

Advantages of Invention

According to the present invention, the easy-to-take solid preparation whose easiness to swallow has been improved (or, that has an excellent easiness to swallow) can be easily produced by means of a continuous tableting machine conventionally used without using any specialized device, means or operation.

Furthermore, as the "easy-to-take" property due to the outer layer-forming processing is obtained only by means of mixing and dry compression-molding of the powder in the present invention, it is possible to produce the easy-to-take solid preparation without going through any wet condition when the inner core tablet has been obtained by compression-molding the core-molding material in the dry process. As a result, the functional or active ingredient can be used even if their stability for the solvent is low.

Furthermore, the solid preparation having a relatively thick outer layer can be easily produced in the dry process.

Due to the "thickness" of the outer layer, slipperiness can be maintained and easiness to swallow can be improved.

EMBODIMENTS FOR CARRYING OUT THE INVENTION

The present invention relates to a dry-process method for the production of an easy-to-take solid preparation wherein an inner core tablet is coated with a compression-molded outer layer-forming agent (an outer layer) comprising a gelling agent that will show slipperiness when it is brought into contact with water, comprising loading separately or simultaneously the inner core tablet and powder of the outer layer-forming agent to a mortar inner surface, the bottom end surface of an upper-pestle, and the top end surface of a lower-pestle, and subsequently compression-molding them.

According to the present method, the inner core tablet may be prepared using the core-molding material by any means or method known for those skilled in the art, preferably being obtained by compression-molding the core-molding material in the dry process. The inner core tablet and the powder of the outer layer-forming agent may be loaded after a lubricant has been applied to the mortar inner surface, and the surfaces of the upper-pestle and the lower-pestle.

In the method according to the present invention, the mortar, the upper-pestle, and the lower-pestle are a member for compressing the inner core tablet and the outer layer-forming agent along the four directions, so as to mold the easy-to-take solid preparation wherein the inner core tablet is coated with the compression-molded outer layer-forming agent. They comprise any other members that are named differently in any other powder compression-molding machines or devices as long as they have substantially the same functions and/or properties as the above ones.

The method according to the present invention does not need any complicated machine, and it can be therefore carried out using such a simple tableting machine as disclosed in the present specification or the rotary-type nucleated-tableting machine conventionally used.

Each process of loading the inner core tablet and powder of the outer layer-forming agent to the mortar inner surface, the bottom end surface of the upper-pestle, and the top end surface of the lower-pestle, etc. may be performed by any means or method known for those skilled in the art depending on the production machine used and the like. For example, the loading of the inner core tablet and powder of the outer layer-forming agent to the mortar inner surface, the bottom end surface of the upper-pestle, and the top end surface of the lower-pestle may be simultaneously or separately carried out by using any appropriate means, or the powder of the outer layer-forming agent may be loaded repeatedly a few times. For example, the powder of the outer layer-forming agent is loaded, followed by the loading of the inner core tablet, and then followed by the loading of the powder of the outer layer-forming agent again. Furthermore, compression-molding of the inner core tablet and the powder of the outer layer-forming agent may be carried out all at once.

The gelling agent that will show slipperiness when it is brought into contact with water according to the present invention means a material that will form a slippery surface of a solid tablet under the moisture condition in the oral cavity when it is taken without water so as to promote the slipperiness of the tablet itself. Such promotion of the slipperiness of the tablet will also make the tablet easy to swallow even when it is taken with water.

The representative examples of the gelling agent include the water-soluble polymer that is selected from the group consisting of sodium carboxylmethylcellulose, sodium alginate, carrageenan, xanthan gum and gelatin. The water-soluble polymer may be naturally-occurring or synthetic one.

The outer layer-forming agent may comprise the gelling agent only, or further comprise other ingredients as long as they will not inhibit the function of the gelling agent. For example, any material known as a lubricant in the art, for example, those selected from the group consisting of calcium stearate, magnesium stearate and sucrose fatty acid ester may be comprised in the outer layer-forming agent so as to obtain the advantage that tableting trouble will not likely occur. The outer layer-forming agent may comprise one or more water-soluble sugar or sugar alcohol known in the art, such as those selected from the group consisting of erythritol, xylitol, mannitol, sorbitol, lactitol, isomalt and maltitol so as to reduce the adhesiveness and to improve easiness to swallow of the tablet. These ingredients other than the gelling agent may be usually comprised less than 99% by weight, preferably less than 98% of the whole outer layer-forming agent.

The "powder" in the present invention means the aggregate of solid particulates, which may include powder having finer size or shape than granules or grains. The whole or a part of the surface of the solid preparation may be in the coated condition according to the present invention.

The ingredients comprised in the powder of the outer layer-forming agent and the core-molding material may be used as they are, or the powder of the outer layer-forming agent and the core-molding material may be prepared by any means or method known in the art such as a dry granulation process, a wet granulation process and the like.

The dry granulation process includes crushing granulation and roll-compressing method, comprising the steps of compressing each powder components into small bulks with a pressure, and appropriately crushing and granulating them, for example.

On the other hand, the wet granulation process is a method in which each component is dispersed in the presence of water, and the dispersion is dried to form complexes. As specific examples of the wet granulation process, spray methods such as spray drying, tumbling granulation, agitation granulation and fluidized-bed granulation; freeze-drying method; kneading granulation, and the like can be mentioned. They can be produced by any of these methods known to a person skilled in the art.

The easy-to-take solid preparation produced by the method according to the present invention is an oral formulation that is called the "nucleated tablet" as well, and has uses, for example, as various foods such as supplemental foods, nutrition function foods and health foods; and as pharmaceuticals.

The core-molding material in the present invention may therefore optionally comprise various components known for those skilled in the art depending on the above uses.

For use as the foods, for example, it may comprise various nutritional components such as proteins, carbohydrates, lipids and minerals; components for health foods such as various extracts from microorganisms, plants and animals; various vitamins and their derivatives; and designated or existing additives according to Food Sanitation Law, Art. 10; and other components acceptable as a food component (a food additive) listed in a list of general additives for food and drink, such as acidulants, sweeteners, excipients, surfactants, lubricants, auxiliary agents, corrigents, flavoring agents, colorants, and stabilizing agents.

For use as the pharmaceuticals, for example, it may comprise in addition to a medicinal or active ingredient, other any pharmaceutically acceptable components, such as excipients, surfactants, lubricants, auxiliary agents, acidulants, sweeteners, corrigents, flavoring agents, colorants, and stabilizing agents, when needed. As these optional components, for example, appropriate ingredients described in "Japanese Pharmaceutical Excipients Directory" (YAKUJI NIPPO LIMITED) or the Japanese Pharmacopoeia; designated or existing additives according to Food Sanitation Law, Art. 10; natural flavor; and additives listed in a list of general additives for food and drink can be used. There is no limitation in the kind of the medicinal ingredient and the above auxiliaries. Also, the blending ratios of each optional ingredient (component) are not particularly limited as long as the desired effects of the present invention are brought about, and the blending ratios can properly be determined by those skilled in the art.

There is no limitation on an application or kind of the medicinal ingredients, which may include, for example, agents affecting each organ such as the central nervous system, peripheral nervous system, a sensory organ, a circulatory organ, a respiratory organ and a digestive organ and an urogenital organ; hormone drug; agents affecting metabolism such as a vitamin drug, an analeptic, an agent affecting blood and body fluid; agents affecting the function of tissue and cell such as an agent activating cellular function, an agent affecting tumors, an radioactive medicine, an anti-allergic agent; medicines based on a medical prescription relating to herbal medicines and Chinese medicines; antibiotics; agents for chemotherapy, biological drug; agents for pathogenic organisms such as parasites; agents for formulation use, diagnosis, public health and in-vitro diagnosis.

Those skilled in the art may optionally select the various conditions in the processes of the production method according to the present invention, such as pressure and time of the compression-molding, and amounts of the outer layer-forming agent and the core-molding material, depending on the scale and kind of the machine to be used in the method, the size and application of a desired easy-to-take solid preparation and the like. For example, tablet compression force in the compression-molding usually ranges from 2 to 100 kN.

There is no limitation on the size, shape and the like of the easy-to-take solid preparation according to the present invention. It is usually within a range of from 3 to 20 mm in diameter and of from 15 to 2000 mg in weight. And, the inner core tablet usually has a diameter with a range of from 1.8 to 18 mm and a weight with a range of from 10 to 1800 mg. They may have any shape known for those skilled in the art such as those of a flat with bevel-edge tablet and a truly-flat tablet. The thickness of the outer layer (coating) consisting of the outer layer-forming agent ranges from about 0.1 to about 5 mm. These values can be determined by any method known for those skilled in the art.

The present invention further relates to the easy-to-take solid preparation that is produced by any one of the above methods; and the powder composition for coating a solid preparation for use as the outer layer-forming agent in the above methods, especially that comprising the water-soluble polymer and water-soluble sugar or sugar alcohol. A preferable example of the composition comprises sodium carboxylmethylcellulose as the water-soluble polymer, and erythritol, xylitol, mannitol or maltitol as the sugar alcohol.

In addition, contents of all related art documents cited in the present specification are incorporated herein by reference.

Hereinafter, the present invention will more specifically be described with reference to Examples. However, the present invention is not considered to be limited to the Examples.

[Evaluation on Hardness, Thickness of the Outer Layer, Slipperiness and Adhesiveness]

Values of the hardness, thickness of the outer layer, slipperiness and adhesiveness of the tablets obtained in the Examples and Comparative Example were measured based on the following conditions/methods.

Hardness: Hardness (N) was measured with a digital Kiya hardness tester (Fujiwara Scientific Company Co., Ltd.). The measurement for the hardness was repeated six times for each tablet, and an average value thereof was regarded as a measurement result.

Thickness of the outer layer: The tablet was fractured and thickness of the resulting cross section was measured with a loupe equipped with ×10 scale (0.1 mm per scale). An average value was regarded as a measurement result. In case where it was hard to distinguish the outer layer from the inner core tablet, an edible dye was added in advance into the inner core tablet, and the thickness of the outer layer was measured.

Slipperiness: Three men and women, respectively (six in total) took the tablet without water, and slipperiness was evaluated in accordance with four-stage criteria below:
4: slipperiness is maintained and very easy to swallow
3: slippery and easy to swallow
2: slightly slippery but hard to swallow
1: hardly slippery and hard to swallow Adhesiveness: Three men and women, respectively (six in total) took the tablet without water, and adhesiveness was evaluated in accordance with three-stage criteria below:
3: not adhered to the inner of an oral cavity
2: slightly adhered to the inner of an oral cavity
1: strongly adhesive to the inner of an oral cavity Example 1

18.0 g of lactose (FlowLac90, MEGGLE JAPAN Co., LTD) and 2.0 g of hydroxypropylcellulose (HPC-SSL-SFP, NIPPON SODA CO., LTD.) were mixed to give a mixture. The resulting mixture was then subjected to tableting at a tablet compression force of 4 kN with a simple tableting machine (HANDTAB-100, ICHIHASHI-SEIKI Co., Ltd.) to thereby obtain an inner core tablet (a truly-flat tablet) having a diameter of 7.6 mm and a weight of 210 mg, wherein a small amount of calcium stearate (Taihei Chemical Industrial Co. Ltd.) had been applied in advance to a mortar inner surface, and the surfaces of an upper-pestle and a lower-pestle in the above tableting machine.

210 mg of the resulting inner core tablet and 40 mg of the outer layer-forming agent (the outer layer) of sodium carboxylmethylcellulose (CMC Daicel, Daicel FineChem Ltd.) were loaded to the simple tableting machine (HANDTAB-100, ICHIHASHI-SEIKI Co., Ltd.) and subjected to tableting at a tablet compression force of 12 kN to thereby obtain a nucleated tablet (a truly-flat tablet) having a diameter of 8.0 mm and a weight of 250 mg, wherein a small amount of calcium stearate (Taihei Chemical Industrial Co. Ltd.) had been applied in advance to the mortar inner surface, and the surfaces of the upper-pestle and the lower-pestle in the above tableting machine.

Example 2

A nucleated tablet (a truly-flat tablet) having a diameter of 8.0 mm and a weight of 250 mg was obtained by the same way as in Example 1 except that 40 mg of xanthan gum (KELTROL CG, SANSHO CO., LTD.) was used as the outer layer.

Example 3

A nucleated tablet (a truly-flat tablet) having a diameter of 8.0 mm and a weight of 250 mg was obtained by the same way as in Example 1 except that 40 mg of sodium alginate (JUNSEI CHEMICAL CO., LTD.) was used as the outer layer.

Example 4

A nucleated tablet (a truly-flat tablet) having a diameter of 8.0 mm and a weight of 250 mg was obtained by the same way as in Example 1 except that 40 mg of carrageenan (CSL-1, San-Ei Gen F.F.I., Inc.) was used as the outer layer.

Example 5

18.0 g of lactose (FlowLac90, MEGGLE JAPAN Co., LTD) and 2.0 g of hydroxypropylcellulose (HPC-SSL-SFP, NIPPON SODA CO., LTD.) were mixed to give a mixture. The resulting mixture was then subjected to tableting at a tablet compression force of 4 kN with the simple tableting machine (HANDTAB-100, ICHIHASHI-SEIKI Co., Ltd.) to thereby obtain an inner core tablet (a truly-flat tablet) having a diameter of 7.6 mm and a weight of 210 mg, wherein a small amount of calcium stearate (Taihei Chemical Industrial Co. Ltd.) had been applied in advance to a mortar inner surface, and the surfaces of an upper-pestle and a lower-pestle in the above tableting machine.

4 g of erythritol (Erythritol T, Mitsubishi-Chemical Foods Corporation) and 1 g of sodium carboxylmethylcellulose (CMC Daicel, Daicel FineChem Ltd.) were mixed to give a mixture for an outer layer.

210 mg of the resulting inner core tablet and 40 mg of the mixture for the outer layer were loaded to the simple tableting machine (HANDTAB-100, ICHIHASHI-SEIKI Co., Ltd.) and subjected to tableting at a tablet compression force of 12 kN to thereby obtain a nucleated tablet (a truly-flat tablet) having a diameter of 8.0 mm and a weight of 250 mg, wherein a small amount of calcium stearate (Taihei Chemical Industrial Co. Ltd.) had been applied in advance to the mortar inner surface, and the surfaces of the upper-pestle and the lower-pestle in the above tableting machine. The thickness of the resulting tablet was about 3.6 mm, and a coating layer (the outer layer) consisting of the outer layer-forming agent had thickness of about 0.2 mm on an average in upper and lower sections of the tablet.

Example 6

A nucleated tablet (a truly-flat tablet) having a diameter of 8.0 mm and a weight of 250 mg was obtained by the same way as in Example 5 except that 210 mg of the inner core tablet and 90 mg of the mixture for the outer layer were used. The thickness of the resulting tablet was about 4.4 mm, and a coating layer (the outer layer) consisting of the outer layer-forming agent had thickness of about 0.6 mm on an average in upper and lower sections of the tablet.

Example 7

A nucleated tablet (a truly-flat tablet) having a diameter of 8.0 mm and a weight of 250 mg was obtained by the same way as in Example 5 except that 4 g of xylitol (Xylite fine powder, Mitsubishi-Chemical Foods Corporation) and 1 g of sodium carboxylmethylcellulose (CMC Daicel, Daicel Fine-Chem Ltd.) were mixed to give a mixture for the outer layer.

Comparative Example 1

18 g of lactose (FlowLac90, MEGGLE JAPAN Co., LTD) and 2 g of hydroxypropylcellulose (HPC-SSL-SFP, NIPPON SODA CO., LTD.) were mixed to give a mixture. The resulting mixture was then subjected to tableting at a tablet compression force of 8 kN with the simple tableting machine (HANDTAB-100, ICHIHASHI-SEIKI Co., Ltd.) to thereby obtain a flat with bevel-edge tablet having a diameter of 8.0 mm and a weight of 250 mg, wherein a small amount of calcium stearate (Taihei Chemical Industrial Co. Ltd.) had been applied in advance to the mortar inner surface, and the surfaces of the upper-pestle and the lower-pestle in the above tableting machine.

Tablet Compression Force, Tablet Hardness, Slipperiness and Adhesiveness of each tablet produced in the above Examples are shown in Table 1.

TABLE 1

| | Ex. 1 | Ex. 2 | Ex. 3 | Ex. 4 | Ex. 5 | Ex. 6 | Ex. 7 | Comp. Ex. 1 |
|---|---|---|---|---|---|---|---|---|
| Tablet Compression Force (kN) | 12 | 12 | 12 | 12 | 12 | 12 | 12 | 8 |
| Tablet Hardness (N) | 120 | 117 | 103 | 114 | 127 | 128 | 132 | 82 |
| Slipperiness | 3 | 3 | 3 | 3 | 3 | 4 | 3 | 1 |
| Adhesiveness | 2 | 2 | 1 | 2 | 3 | 3 | 3 | 3 |

The results shown in Table 1 demonstrate that the nucleated tablets produced in Examples 1 to 4 were more slippery and easier to swallow, which were produced using the water soluble polymer in the outer layer, than the inner core tablet (Comparative Example 1). Examples 5 to 7 showed that trituration of the water soluble polymer in the outer layer with the sugar alcohol reduced Adhesiveness and improved easiness to swallow of the tablets. Examples 5 and 6 further showed that the tablet is maintained to be slippery and become very easy to swallow by increasing the thickness of the outer layer.

INDUSTRIAL APPLICABILITY

The present invention significantly contributes to research and development of the method for the production of the easy-to-take solid preparation, the easy-to-take solid preparation and the like.

The invention claimed is:

1. A dry-process method for the production of an easy-to-take solid preparation, comprising:
   loading separately or simultaneously an inner core tablet and powder of an outer layer-forming agent comprising a gelling agent to a mortar inner surface, a bottom end surface of an upper-pestle, and a top end surface of a lower-pestle, and
   compression-molding the outer layer forming agent comprising the gelling agent onto the inner core tablet so that the gelling agent shows slipperiness when brought into contact with water,
   wherein the outer layer-forming agent further comprises a water-soluble sugar or sugar alcohol and wherein the gelling agent comprises at least one kind of a water-soluble polymer.

2. The method according to claim 1, wherein a core-molding material in the inner core tablet is subjected to compression-molding in a dry process.

3. The method according to claim 1, wherein the inner core tablet and the powder of the outer layer-forming agent are loaded after a lubricant has been applied to the mortar inner surface and the surfaces of the upper-pestle and the lower-pestle.

4. The method according to claim 1, wherein the water-soluble polymer is selected from the group consisting of sodium carboxylmethylcellulose, sodium alginate, carrageenan, xanthan gum and gelatin.

5. The method according to claim 4, wherein the water-soluble polymer is sodium carboxylmethylcellulose.

6. The method according to claim 1, wherein the outer layer-forming agent further comprises a lubricant.

7. The method according to claim 6, wherein the lubricant is selected from the group consisting of calcium stearate, magnesium stearate and sucrose fatty acid ester.

8. The method according to claim 1, wherein the sugar or sugar alcohol is erythritol, xylitol, mannitol or maltitol.

* * * * *